United States Patent [19]

Takahashi et al.

[11] 4,322,129
[45] Mar. 30, 1982

[54] ILLUMINATING LIGHT CONTROL DEVICE FOR ENDOSCOPE

[75] Inventors: Nagashige Takahashi, Tokyo; Shinichi Harada, Urawa; Eiji Yamamori, Tokyo, all of Japan

[73] Assignee: Kabushiki Kaisha Medos Kenkyusho, Tokyo, Japan

[21] Appl. No.: 125,052

[22] Filed: Feb. 27, 1980

[30] Foreign Application Priority Data

Mar. 1, 1979 [JP] Japan .............................. 54/26408[U]
Mar. 1, 1979 [JP] Japan .............................. 54/26409[U]

[51] Int. Cl.³ ............................................. G05D 25/02
[52] U.S. Cl. ................................ 350/269; 350/96.26; 350/273
[58] Field of Search ............... 350/273, 74, 269, 96.25, 350/96.26, 96.27; 128/4, 6, 22; 356/52

[56] References Cited

U.S. PATENT DOCUMENTS

| 2,461,379 | 2/1949 | Hamilton | 350/273 X |
| 2,774,276 | 12/1956 | Glasser et al. | 350/273 X |
| 3,329,074 | 7/1967 | Gosselin | 128/4 |
| 3,599,630 | 8/1971 | Sato et al. | 350/96.26 X |
| 3,698,099 | 10/1972 | Matsura | 350/96.26 X |
| 4,165,919 | 8/1979 | Little | 350/273 |

Primary Examiner—John K. Corbin
Assistant Examiner—Matthew W. Koren
Attorney, Agent, or Firm—Sughrue, Mion, Zinn, Macpeak and Seas

[57] ABSTRACT

An illuminating light control device for an endoscope for controlling both the intensity and hue of illuminating light over a wide range. A shutter mechanism is disposed between a discharge lamp light source and the receiving end of an optical fiber bundle. The shutter mechanism may be moved between at least three positions. At the first position, the light is allowed to pass directly from the light source to the optical fiber bundle and the light source is allowed to vary between its maximum and minimum limits. At the minimum limit, the shutter mechanism disposes a transmission light control means in the light path and the light source is returned to its maximum limit whereupon the output light to the optical fiber bundle is the same before the change as afterward. The light source can then be varied again between its maximum and minimum limits thereby effectively doubling the range of light output intensity. The shutter can also be moved to a position which blocks the optical path for a photographing operation.

14 Claims, 6 Drawing Figures

ILLUMINATING LIGHT CONTROL DEVICE FOR ENDOSCOPE

BACKGROUND OF THE INVENTION

The invention relates to a device for controlling the intensity and hue of illuminating light introduced through an optical fiber bundle of an endoscope for illuminating a part of a human body. More particularly, the invention relates to a device in which the mechanism and arrangement for illuminating light control is simplified and the light intensity control range is relatively large.

In observing a deep part of a body cavity or in photographing such with an endoscope of the general type to which the invention relates, it is necessary to illuminate the part to be examined with light introduced through the optical bundle of the endoscope. In photographing the body cavity being examined, the intensity of light thus introduced should be relatively high for the picture to have satisfactory detail. However, for observing the body cavity with the eye for relatively long periods of time, it is undesirable that the light have such a high intensity as it will thermally stimulate the body cavity.

In view of this, an illuminating light intensity control device has been previously employed in which, in observing the body cavity with the naked eye, an optical filter is inserted in the illuminating light path while for photographing the body cavity, the optical filter is retracted from the illuminating light path. In such an illuminating light intensity control device, the timing of the optical filter going in and out of the light path is made synchronous with the operation of the shutter in the photographing operation in order to minimize the thermal stimulus to the body cavity due to the high intensity light. Therefore, the illuminating light intensity control means is necessarily intricate in arrangement.

Moreover, for observing the body cavity with the naked eye, if the surface being observed is excessively bright, then the operator's eye may be dazzled, the contrast of the part being observed is lowered and, accordingly, it is difficult to satisfactorily observe the minute affected part of the body cavity. Thus, it is desirable that the intensity of the illuminating light be controlled according to the position and condition of a part to be examined of the body cavity. In the case where an incandescent lamp is employed as the light source, the intensity of illuminating light can be controlled over a relatively wide range by a light control device such as a voltage control device. However, in this case also, the light intensity range is limited because color hue at light emitted from an incandescent is affected by the reduction of the light intensity. Especially in the case where a discharge lamp is employed as the light source, the electric power control range is limited because the discharge lamp will properly emit light only over a relatively narrow range of input power so that the illuminating light intensity control range is correspondingly very narrow.

In order to be practical and suitable for actual clinical use, a device which is employed to vary the illuminating light intensity of an incandescent lamp should cause the color hue rendering to be satisfactory and a device used with a discharge lamp should be capable of varying the output intensity over a wide range.

Sometimes locating and observing an affected part of the body cavity can be readily achieved by changing the hue of the illuminating light according to the conditions of the affected part. Therefore, it is desirable that the control device be capable of hue control as well as intensity control.

In view of the foregoing, an object of the invention model is to provide an illumination light control device for an endoscope which can effectively control the intensity and hue of illuminating light and is simple in construction.

SUMMARY OF THE INVENTION

These, as well as other objects of the invention, are met by an illuminating light intensity control device for an endoscope including a light source which is preferably a discharge lamp, an optical fiber bundle, a shutter blade which is disposed so as to be movable in and out of an optical path which extends from the light source to a light receiving end face of the optical fiber bundle. The shutter blade includes transmission light control means provided in a portion of the shutter blade which is disposed in the optical path for a predetermined position of the shutter blade. There is also provided moving means coupled to the shutter blade for providing a shutter operation and for disposing and holding the shutter blade in the position in which the transmission light control means is in at least a portion of the optical path. The shutter blade can be moved to any of three positions. These are a position in which the light is completely blocked between the light source and the optical fiber bundle, a position in which the transmission light control means is disposed in the light path, and a position in which light can pass directly from the light source to the optical fiber bundle without passing through any light changing medium therebetween. Means is provided for varying the output light intensity from the light source between minimum and maximum limits. At the minimum intensity of the light source, the moving means operates to move the shutter means to the position where the transmission light control means is disposed and the light path. At that point, the intensity of the light source is returned to the maximum value. The transmission light control means is preferably constructed and has a light transmission factor which makes the amount of light passed immediately after the transmission light control means is disposed in the light path to be the same as that emitted from the light source at the minimum limit. The light source can then be again varied between the maximum and minimum limits with the transmission light control means disposed in the light path whereby the effective light intensity range of the light source is doubled.

The transmission light control means may be provided as a group of small holes, a mesh window, or an optical filter. Moreover, hue changing means can be provided as well such as through additional apertures in the shutter member. The shutter member may be provided as a shutter blade which is pivoted at one end and operated by an electrical mover such as a tri-state solenoid device or may be provided as a rotary disc the position of which is changed in accordance with an input control signal by a device such as a stepper motor.

DESCRIPTION OF THE PREFERRED EMBODIMENTS

The invention will be described with reference to its preferred embodiments shown in the accompanying drawings.

Figure 1:
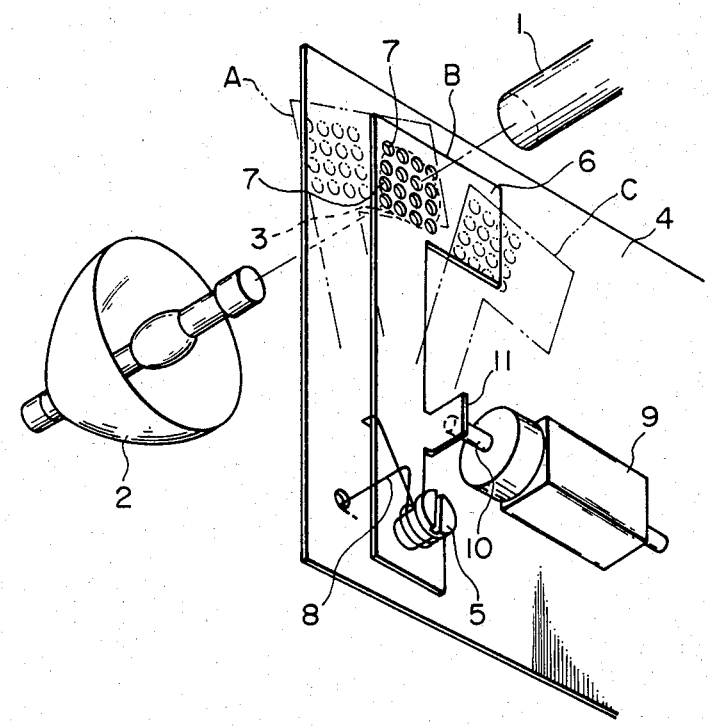
FIG. 1 is a perspective view of a preferred embodiment of an illuminating light control device.

FIG. 1 is a perspective view of a preferred embodiment of an illuminating light control device according to the invention. A substrate 4 having an optical window 3 is provided in an optical path extending from a light source 2, which is preferably a discharge lamp, to the light receiving end face of an optical fiber bundle 1 in an endoscope. The substrate 4 is provided with a shutter blade 6. One end portion of the shutter blade 6 is rotatably supported on a supporting shaft 5 on the substrate 4 in such a manner that the other free end portion can move freely in and out of the optical path which extends through the optical window. The shutter blade 6 includes a widened portion which extends in the direction that the blade swings. In the widened portion of the shutter blade 6, a transmission light intensity control means is provided. More specifically, the transmission light intensity control means is implemented in the embodiment of FIG. 1 by forming a number of small holes 7 in the widened portion of the shutter blade 6. The transmission light intensity control means may also be provided as a mesh-like member cut into or bonded to the blade or an optical filter bonded thereto instead of the small holes 7 or other such intensity control means so long as it can reduce the intensity of light passing therethrough by several tens of percent.

The shutter blade has a protrusion 11 which extends perpendicularly from the middle portion of the shutter blade. A spring 8 is coupled to the supporting shaft 5 to bias the shutter blade 6 in the clockwise direction as shown in the figure so that the protrusion 11 is held in abutment against the operating rod 10 of a tri-stable electromagnetic mechanism 9 at all times. The shutter blade 6 can be swingably moved to any of three positions A, B and C as indicated by the solid and chain lines in FIG. 1 as the rod 10 of the electromagnetic mechanism 9 is operated.

Figure 2:
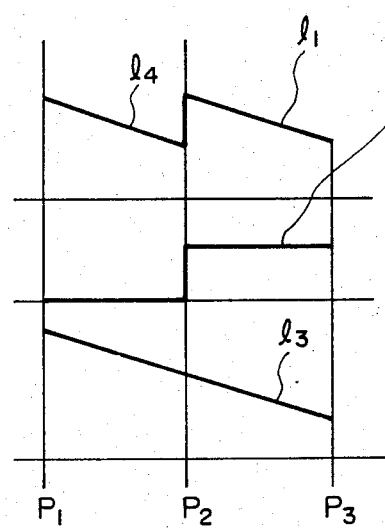
FIG. 2 is a diagram for a description of the operation of the illuminating light intensity control of the device shown in FIG. 1.

FIG. 2 is a characteristic diagram indicating the control of the intensity of illuminating light for diagnosis, hereinafter referred to as "diagnosis illuminating light intensity control" when applicable. In FIG. 2, reference character $l_1$ designates a graph of the output of the light source, $l_2$ indicates the timing of the transmission light intensity control means going in and out of the optical path extending from the light source to the light receiving end face of the optical fiber bundle, and $l_3$ the final light output intensity to the optical fiber bundle.

Figure 3:
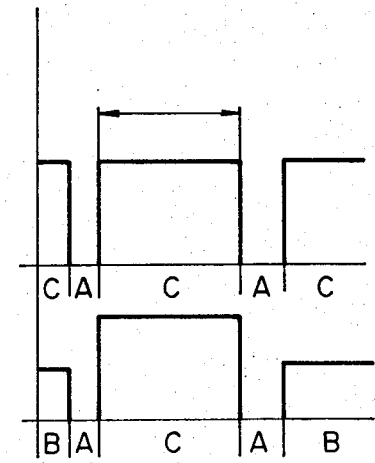
FIG. 3 is a sequence diagram for a description of a photographing operation effected with the device of the invention.

FIG. 3 is a sequence diagram indicating a typical light intensity control operation for photographing the body cavity which is effected with the device according to the invention. The upper part of FIG. 3 illustrates the case where the transmission light intensity control means is out of the optical path while the lower part corresponds to the case where the transmission light intensity control means is in the optical path.

In the device constructed as described above, for maximum illuminating intensity, a control signal is applied to the electromagnetic mechanism 9 which causes the rod 10 to be maximally retracted into the electromagnetic mechanism body and the shutter blade 6 is set at a first position designated by reference character C in FIG. 1 so that light from the light source 2 reaches directly through the optical window 3 to the light receiving end face of the optical fiber bundle 1. Then, the intensity of illuminating light from the light source 2 may be adjusted as indicated by the line $l_4$ in FIG. 2 so that the diagnosis illuminating light intensity is changed to values lying along the first half of the characteristic line $l_3$ in FIG. 2 between $P_1$ and $P_3$.

When the light intensity adjustment of the light source 2 reaches its limit at the lower end of the light intensity variational range of the light source 2 at $P_2$, the control signal applied to the electromagnetic mechanism 9 is changed so that the rod 10 extends to its intermediate position. As a result, the shutter blade 6 is swung to the second position designated by reference character B and indicated by the solid line and the group of small holes 7 formed in the widened portion of the shutter blade 6 is placed in the optical path extending through the optical window 3.

As soon as the transmission light intensity control means is placed in the optical path as described above, the intensity of light emitted by the light source is increased or restored as indicated by the middle part of the line $l_1$ at $P_2$ to its limit at the upper end of its intensity range. The intensity of light from the light source may therefore be reduced as before whereby the illuminating light intensity will vary as indicated by the second half of the line $l_3$ in FIG. 2 between $P_2$ and $P_3$. As is thus apparent, the light intensity can be continuously or smoothly reduced.

For photographing the body cavity, the electromagnetic mechanism 9 is driven so that the rod 10 protrudes maximally to swing the shutter blade to a third position designated by reference character A and indicated by a chain line in FIG. 1 thereby to momentarily completely close the optical path. To expose the film, the shutter blade 6 is moved back to the first position A to fully open the optical path. At the end of the film exposure time, the shutter blade, which had fully opened the optical path, is returned to its initial position A again fully closing the optical path.

Figure 5:
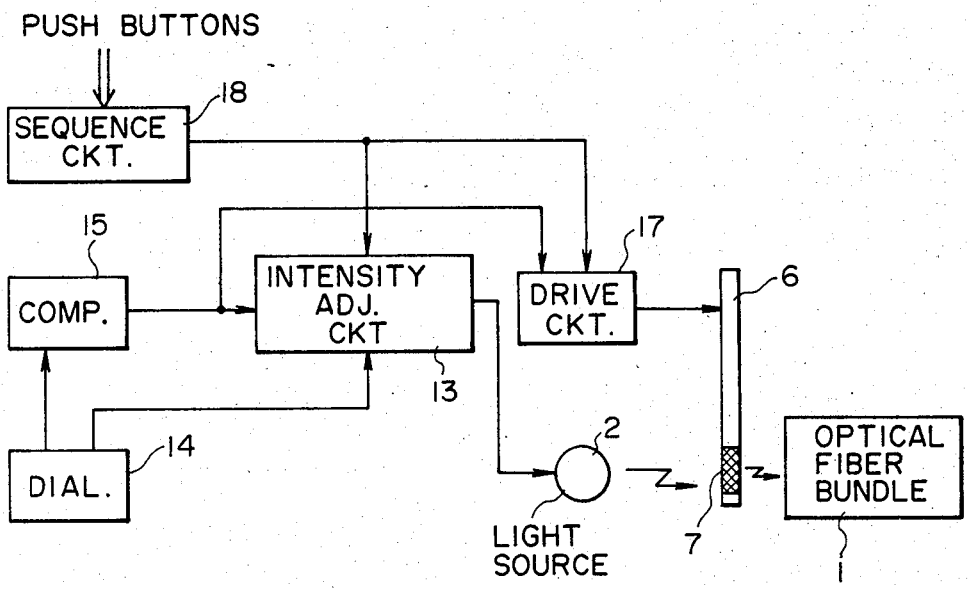
FIG. 5 is a block diagram of a control circuit for use in the light intensity control device of the invention.

FIG. 5 is a block diagram showing the circuitry of an illuminating light intensity control device according to the invention. In FIG. 5, the light source 2 confronts the light receiving end face of the illuminating optical fiber bundle 1 employed so as to apply a pencil of light rays to the light receiving end face of the optical fiber bundle 1. Electric power supplied to the light source 2 is controlled by a lamp light intensity adjusting circuit 13.

The amount of control effected by the lamp light intensity adjusting circuit 13 can be varied by a light intensity adjusting dial 14 which may be an externally operable variable resistor or the like. The dial 14 provides an operational signal which is applied to a comparison circuit 15. The comparison circuit 15 determines whether or not the operational signal satisfies a predetermined condition, described later and, if so, outputs a decision signal. The decision signal is supplied to the lamp light intensity adjusting circuit 13 to instantly change the control operation of the circuit 13.

The drive circuit 17, which drives the electromagnetic mechanism 9, is under the control of a sequence circuit 18 which is in turn controlled by the operation of push-button switches and by the decision signal produced by the comparison circuit 15. The control signal from the sequence circuit 18 is applied further to the lamp light intensity adjusting circuit 13 so that the circuit 13 operates in synchronization with the drive circuit 17. Furthermore, the decision signal produced at the output of the comparison circuit 15 applied to the lamp light intensity adjusting circuit 13 is also applied to the drive circuit 17 so that the lamp light intensity adjusting circuit 13 and the drive circuit 17 are operated synchronously.

With the illuminating light intensity control device of the invention thus constructed, the intensity of light applied to the light receiving end face of the optical fiber bundle 1 is changed as indicated by the characteristic line $l_3$ in FIG. 2. In a first range of from the maximum light intensity point $P_1$ to the intermediate light intensity point $P_2$ in the overall light intensity variable range $P_1$-$P_3$, the amount of electric power supplied from the lamp light intensity adjusting circuit 13 to the light source 2 is controlled by the light intensity dial means 14 so that the intensity of light emitted by the light source 2 is controlled as indicated by the line $l_4$ in FIG. 2. In this operation, the transmission light intensity control means, the group of small holes 7, is not disposed in the optical path between the light source 2 and the light receiving end face of the optical fiber bundle 1. Therefore, the intensity of light emitted by the light source 2 is maintained unchanged at the light receiving end face of the optical fiber bundle 1.

When the intensity of light emitted by the light source is reduced to the minimum value of the intermediate light intensity point $P_2$, which minimum value is determined by the inherent characteristics of the light source 2 such as discharge light emission maintaining power in the case of a xenon lamp, or light source color temperature decrement in the case of an incandescent lamp, the reduction to the minimum value is detected by the comparison circuit. As a result, the decision signal is applied to the drive circuit by the comparison circuit in response to which the light shielding blade 6 is turned by the drive circuit so that the transmission light intensity control means is disposed in the optical path between the light source 2 and the light receiving end face of the optical fiber bundle 1.

The decision signal is applied to the lamp light intensity adjusting circuit 13 also which abruptly increases the intensity of light emitted by the light source at $P_2$ substantially to that at $P_1$. As the intensity of light emitted by the light source 2 is reduced by continuously operating the light intensity adjusting dial 4 as indicated by a characteristic line $l_1$ in FIG. 2, the intensity of light applied to the light receiving end face is as indicated by the characteristic line $l_1$ in FIG. 2.

Besides the dial 4, the control operation of the sequence circuit 8, effected by operating the push-button switches or the like, can selectively determine the ranges $P_1$-$P_2$ and $P_2$-$P_3$ between which the transmission light intensity control means is disposed in and out of the optical path, that is, over the incident light intensity variable range $P_1$-$P_3$. Furthermore, the operation of the sequence circuit 8 can be employed to control the flash operation in which the intensity of the light source 2 is instantly increased to the maximum for the case where the light shielding blade 6 carried out both of the functions of the transmission light intensity control means and the shutter blade in the shutter mode of operation.

As is apparent from the above description, in the device according to the invention, the intensity of light emitted by the light source is controlled in synchronization with the timing of the transmission light intensity control member moving in and out of the optical path between the light source and the light receiving end face of the optical fiber bundle. Therefore the illuminating light intensity can be controlled over a range larger than that of the light source itself. If several transmission light intensity control means having different optical transmissivity properties are used and the intensity of light emitted by the light source is repeatedly controlled over a range defined by the number of transmission light intensity control means employed, then the illuminating light intensity range can be increased to several times the range of the light source alone.

Provision may be made for the transmission light intensity control means to be manually shifted in and out of the optical path. In this case, the device may be designed so that the intensity of light emitted by the light source is changed in response to the detection of the insertion of the transmission light intensity control means thus operated manually. It is not always required that the illumination light intensity be continuously or smoothly changed when the transmission light intensity control means is moved in and out of the optical path. That is, substantially the same effect can be obtained even if the illumination light intensity is changed stepwise.

Figure 4:
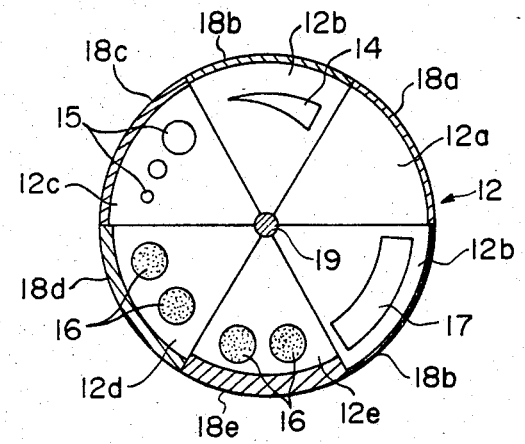
FIG. 4 is a plan view of a shutter blade employed in a second embodiment of a device according to the invention.

FIG. 4 is a plan view of a shutter blade for a second embodiment of an illumination light control device according to the present invention. The shutter blade has a disc-shaped control member 12 and a central shaft 19 which is coupled to a drive mechanism such as a pulse motor (not shown) so that the rotational angular position of the shutter blade can be changed. A shutter blade section 12a, a transmission light intensity control section 12b having a wedge-shaped through hole 14, a transmission light intensity control section 12c having through-holes of differing diameters, hue control sections 12d and 12e provided with color filters 16 of differing hue and saturation, and a control section 12f having a window 17 through which light passes directly for photographing are successively arranged upon the circumferential portion of the control board 12. The control board 12 is disposed between the light source 2 and the light receiving end face of the optical fiber bundle 1. Control section position detecting code portions 18a through 18f are provided in the peripheral portion of the control board for the control sections 12a through 12f, respectively.

Similar to the embodiment shown in FIG. 1, the rotational angular positions of the control sections are controlled by means of a pulse motor or the like while the input power to the light source 2 is changed to control the output intensity of light emitted thereby. For the case where a number of circular through-holes 15 of different diameters are provided in the light intensity control section, the output from light source 2 may be varied over its range several times, once for each of the circular through-holes 15.

The control sections 12d and 12e include the color filters 16 which are disposed in the optical path as described above. For example, if a cyan colored filter is disposed in the optical path, the red walls of the stomach can be illuminated in such a manner that the unevenness thereof appears clearly.

In the second embodiment of the device according to the invention described above, the control sections may be combined and arranged on the control board 12 as desired. In this connection, all that is required is that the chosen control sections be provided in portions of the control board other than that reserved for shutter control. Since the control section position detecting code portions 18a through 18f are provided for detecting the rotational angular positions of the control board, it is not always necessary to arrange the codes as shown in FIG. 4. That is, they may be provided on a member which rotates or moves together with the control board, or a drive source connected to the control board.

As is clear from the above description, in the device according to the invention, a means for controlling the intensity of light transmitted and a means for varying the tone of light transmitted are provided in portions of the shutter blade which can move in and out of the optical path. The transmission light intensity control section can also be put in the optical path and held there. Therefore, a predetermined light intensity variation control range is established. In combination with the means for varying the intensity of light from the light source, the diagnosis illuminating light intensity variation range can be smoothly varied. Furthermore, the hue and saturation of the illuminating light can be varied in accordance with the teachings of the invention. In addition, these elements which are controlled electrically and mechanically are collected at one position. Thus, the device of the invention is advantageous in that its construction is simple and the operation thereof can be controlled with high accuracy.

Figure 6:
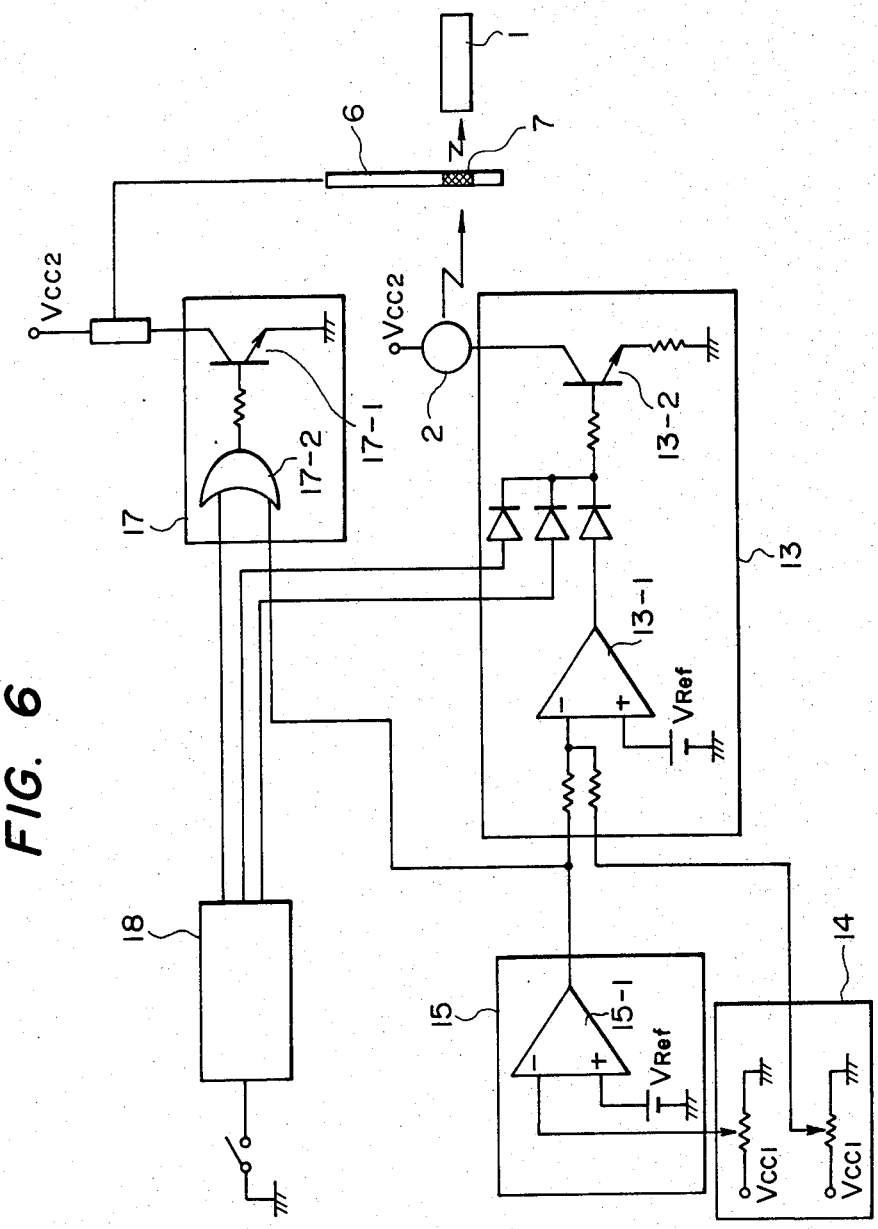
FIG. 6 is a schematic diagram showing a preferred implementation of the control circuit shown in FIG. 5.

Referring now to FIG. 6, there is shown therein in schematic diagram form a preferred implementation of the control circuit shown in FIG. 5. As shown in this diagram, the dial means 14 in FIG. 5 may be implemented as two potentiometers, both of them having one end terminal connected to ground and the other end terminal connected to a positive voltage source having a potential $V_{CC1}$. The wiper contact one of these is connected to one input of a comparator 15-1 of comparator circuit 15, the other input of which is coupled to a reference source having a voltage of $V_{ref}$. The output of comparator 15-1 is coupled through a resistor to one input of operational amplifier 13-1 of the intensity adjustment circuit 13. The wiper contact of the second potentiometer of dial means 14 is coupled through a second resistor to this same input. The other input of the operational amplifier 13-1 is coupled to a second voltage reference source.

The output of operational amplifier 13-1 is coupled through a first diode and resistor to the base input of output transistor 13-2. The emitter of transistor 13-2 is connected through a current limiting resistor to ground while the collector thereof is connected through the light source 2 to a supply voltage $V_{CC2}$.

First and second outputs of sequence circuit 18 are coupled through second and third diodes to the cathode of the first diode coupled to the operational amplifier 13-1. Output signals from sequence circuit 18 to the diodes can set the transistor 13-2 to either stop the flow of current to light source 2 or to operate it at its maximum value for a photographing operation. Another output of sequence circuit 18 is coupled through an OR gate 17-2 of drive circuit 17. The second input to the OR gate 17-2 is the decision signal generated at the output of the comparator 15-1. The output of OR gate 17-2 is coupled through a resistor to the base input of drive transistor 17-1, the collector of which is connected through the latching solenoid or pulse motor which mechanically moves the shutter blade 6 in accordance with the output of OR gate 17-2.

What is claimed is:

1. An illuminating light intensity control device for an endoscope comprising: a light source, an optical fiber bundle, a transmission light control means movable into and out of an optical path extending from said light source to a light receiving end face of said optical fiber bundle, and moving means coupled to said transmission light control means for moving said transmission light control means into at least a portion of said optical path in response to a predetermined minimum intensity of light produced by said light source.

2. The intensity control device as claimed in claim 1 further comprising means for increasing the intensity of light produced by said light source at a time simultaneously when said transmission light control means is disposed in said optical path.

3. The intensity control device as claimed in claim 1 further comprising means for detecting the position of said transmission light control means.

4. The intensity control device of claim 1 wherein said transmission light control means comprises a group of small holes.

5. The intensity control device of claim 1 wherein said transmission light control means comprises a mesh window.

6. The intensity control device of claim 1 wherein said transmission light control means comprises an optical fiber.

7. The intensity control device of claim 1 wherein said light source comprises a discharge lamp.

8. An illuminating light intensity control device for an endoscope comprising: a light source, means for varying the light output of said light source between predetermined minimum and maximum limits, means for determining when said light output is at said minimum limit, means for disposing light intensity reducing means in a light path between said light source and an optical fiber bundle in response to an output signal from said light output determining means indicative of said light output being at said minimum limit, and means for returning the light output of said light source to said maximum limit upon said light intensity reducing means being disposed in said optical path.

9. The intensity control device of claim 8 wherein said light intensity reducing means is chosen so that the intensity of illumination of said optical fiber bundle through said intensity reducing means when said light source is producing light at said maximum limit of said light source is the same as the intensity of illumination of said optical fiber bundle at the minimum light output of said light source when said light intensity reducing means is not disposed in said light path.

10. A method for providing a wide range of light output intensity comprising the steps of: providing a light source having a light output variable between minimum and maximum limits; producing a decision signal when said light output is at said minimum limit, disposing light intensity reducing means in a light path between said light source and utilization means in response to said decision signal, and operating said light source to return said light output to said maximum limit.

11. The method of claim 10 wherein said light intensity reducing means reduces the intensity of illumination of said utilization means at said maximum limit of said light source to the same value as the intensity of illumination received by said utilization means at said minimum limit when said light intensity reducing means is not disposed in said light path.

12. An illuminating light intensity control device for an endoscope comprising: a base member having an aperture therein; a light source; a shutter blade provided at one end and being pivotable between first, second and third positions wherein a first portion of said shutter blade covers said aperture in said first position, a portion of said shutter blade formed as light intensity reducing means covering said aperture in said second position, and said shutter blade being clear of said aperture in said third position; means for varying the intensity of light produced by said light source between said minimum and maximum limits; and means for moving said shutter blade between said first, second and third positions in response to a control signal, wherein the light output passing through said aperture in the second position of said shutter blade at the maximum limit of light source intensity is substantially the same as the light passing through said aperture at the minimum limit of light source intensity in the third position of said shutter blade.

13. The intensity control device of claim 12 wherein said moving means moves said shutter blade from said first position to said third position and back to said first position for a photographing operation.

14. An illuminating light intensity control device as claimed in claim 1, wherein the intensity of light from said light source is adjustable between a maximum intensity and said minimum intensity, and wherein the intensity of illumination received by said optical fiber bundle through said transmission light control means at said maximum light source intensity is substantially equal to the intensity of illumination received by said optical fiber bundle at said minimum light source intensity when said transmission light control means is not disposed in said optical path.

* * * * *